US008409817B2

(12) United States Patent
O'Connor, Jr. et al.

(10) Patent No.: US 8,409,817 B2
(45) Date of Patent: Apr. 2, 2013

(54) METHODS AND COMPOSITIONS FOR DETECTION OF *EHRLICHIA CHAFFEENSIS* (VLPT)

(75) Inventors: Thomas Patrick O'Connor, Jr., Westbrook, ME (US); Eugene Regis Krah, III, Freeport, ME (US); Jill M. Saucier, Gorham, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 13/162,671

(22) Filed: Jun. 17, 2011

(65) Prior Publication Data

US 2011/0250615 A1   Oct. 13, 2011

Related U.S. Application Data

(62) Division of application No. 12/234,188, filed on Sep. 19, 2008, now Pat. No. 7,964,366.

(60) Provisional application No. 60/974,196, filed on Sep. 21, 2007.

(51) Int. Cl.
*G01N 33/53* (2006.01)
*G01N 33/569* (2006.01)
*A61K 39/395* (2006.01)
*A61K 39/00* (2006.01)
*A61K 39/38* (2006.01)
*A61K 39/002* (2006.01)
*A61K 38/00* (2006.01)
*C07K 5/00* (2006.01)
*C07K 16/00* (2006.01)
*C07K 17/00* (2006.01)

(52) U.S. Cl. ............... 435/7.22; 424/151.1; 424/184.1; 424/192.1; 424/265.1; 435/7.1; 530/324

(58) Field of Classification Search ............... 435/7.22, 435/7.1; 424/151.1, 84.1, 192.1, 265.1; 530/324
See application file for complete search history.

(56) References Cited

U.S. PATENT DOCUMENTS

| | | | |
|---|---|---|---|
| 4,275,149 A | 6/1981 | Litman et al. |
| 4,318,980 A | 3/1982 | Boguslaski et al. |
| 4,676,980 A | 6/1987 | Segal et al. |
| 5,192,679 A | 3/1993 | Dawson et al. |
| 5,401,656 A | 3/1995 | Dawson |
| 5,413,931 A | 5/1995 | Dawson et al. |
| 5,726,010 A | 3/1998 | Clark |
| 5,789,176 A | 8/1998 | Dawson et al. |
| 5,869,335 A | 2/1999 | Munderloh et al. |
| 5,928,879 A | 7/1999 | Dumler et al. |
| 5,955,359 A | 9/1999 | Dumler et al. |
| 5,976,791 A | 11/1999 | Mabilat et al. |
| 5,976,860 A | 11/1999 | Coughlin et al. |
| 5,989,848 A | 11/1999 | Dawson |
| 6,015,691 A | 1/2000 | Walker et al. |
| 6,025,338 A | 2/2000 | Barbet et al. |
| 6,034,085 A | 3/2000 | Joshl et al. |
| 6,043,085 A | 3/2000 | Yu et al. |
| 6,204,252 B1 | 3/2001 | Murphy et al. |
| 6,207,169 B1 | 3/2001 | Reed et al. |
| 6,231,869 B1 | 5/2001 | Reed et al. |
| 6,251,872 B1 | 6/2001 | Barbet et al. |
| 6,277,381 B1 | 8/2001 | Reed et al. |
| 6,284,238 B1 | 9/2001 | Coughlin et al. |
| 6,306,394 B1 | 10/2001 | Murphy et al. |
| 6,306,402 B1 | 10/2001 | Reed et al. |
| 6,355,777 B1 | 3/2002 | Walker et al. |
| 6,392,023 B1 | 5/2002 | Walker et al. |
| 6,403,780 B1 | 6/2002 | Walker et al. |
| 6,458,942 B1 | 10/2002 | Walker et al. |
| 6,593,147 B1 | 7/2003 | Barbet et al. |
| 7,087,372 B2 | 8/2006 | Lawton et al. |
| 7,204,992 B2 | 4/2007 | McBride |
| 7,407,770 B2 | 8/2008 | O'Connor |
| 7,445,788 B2 | 11/2008 | Lawton et al. |
| 7,449,191 B2 | 11/2008 | Lawton et al. |
| 7,741,059 B2 | 6/2010 | O'Connor et al. |
| 7,892,568 B2 | 2/2011 | O'Connor et al. |
| 7,964,366 B2 | 6/2011 | O'Connor et al. |
| 2002/0064531 A1 | 5/2002 | Walker et al. |
| 2002/0064535 A1 | 5/2002 | Reed et al. |
| 2002/0068343 A1 | 6/2002 | Reed et al. |
| 2002/0086984 A1 | 7/2002 | Reed et al. |
| 2002/0115840 A1 | 8/2002 | Walker et al. |
| 2002/0120115 A1 | 8/2002 | Rikihisa et al. |
| 2002/0132789 A1 | 9/2002 | Barbet et al. |
| 2002/0160432 A1 | 10/2002 | Lawton et al. |
| 2002/0177178 A1 | 11/2002 | Lawton et al. |
| 2003/0119082 A1 | 6/2003 | Lawton et al. |
| 2003/0129680 A1 | 7/2003 | O'Connor |
| 2003/0194756 A1 | 10/2003 | O'Connor |
| 2003/0194757 A1 | 10/2003 | O'Connor et al. |
| 2005/0124015 A1 | 6/2005 | O'Connor et al. |
| 2006/0189537 A1 | 8/2006 | O'Connor |
| 2006/0211062 A1 | 9/2006 | O'Connor |
| 2006/0234322 A1 | 10/2006 | Krah et al. |
| 2007/0020733 A1 | 1/2007 | Lawton |
| 2009/0081695 A1 | 3/2009 | O'Connor et al. |
| 2011/0033487 A1 | 2/2011 | McBride |

FOREIGN PATENT DOCUMENTS

| | | |
|---|---|---|
| EP | 1581638 | 9/2007 |
| WO | 97/45540 | 12/1997 |

(Continued)

OTHER PUBLICATIONS

Ohashi et al., "Immunodominant Major Outer Membrane proteins for *Ehrlichia chaffeensis* are Encoded by the Polymorphic Multigene Family", Infection and Immunity, 66:132-139 (1998).

Ohashi et al., "Cloning and characterization of Multigenes Encoding the Immunodominant 30-Kilodalton Major Outer Membrane Proteins of *Ehrlichia canis* and Application of the Recombinant Protein for Serodiagnosis", Journal of Clinical Microbiology, 36:2371-2680 (1998).

Yu et al., Genetic Diversity of the 28-Kilodalton Outer Membrane Protein Gene in Human Isolates of *Ehrlichia chaffeensis*:, Journal of Clinical Microbiology, 37:1137-1143 (1999).

McBride et al., "Molecular Cloning of the Gene for a Conserved Major Immunoreactive 28-Kilodalton Protein of *Ehrlichia canis*: a Potential Serodiagnostic Antigen", Clinical and Diagnostic Laboratory Immunology, 62:392-399 (1999).

(Continued)

*Primary Examiner* — Vanessa L Ford
*Assistant Examiner* — Nina Archie
(74) *Attorney, Agent, or Firm* — McDonnell Boehnen Hulbert & Berghoff LLP

(57) ABSTRACT

The invention provides methods and compositions for the detection of *Ehrlichia chaffeensis*.

24 Claims, 1 Drawing Sheet

FOREIGN PATENT DOCUMENTS

| WO | 99/13720 | 3/1999 |
|---|---|---|
| WO | 00/12688 | 3/2000 |
| WO | 00/65064 | 11/2000 |
| WO | 01/85949 | 11/2001 |
| WO | 02/057794 | 7/2002 |
| WO | 03/087758 | 10/2003 |
| WO | 2006/107924 | 10/2006 |
| WO | 2006/138509 | 12/2006 |
| WO | 2008/112077 | 9/2008 |
| WO | 2009/039413 | 3/2009 |
| WO | 2009039414 | 3/2009 |
| WO | 2009102509 | 8/2009 |

OTHER PUBLICATIONS

Yu et al., "Comparison of *Ehrlichia chaffeensis* Recombinant Proteins for Serologic Diagnosis of Human Monocytotropic Ehrlichiosis", Journal of Clinical Microbiology, 37:2568-2575 (1999).
Yu et al., "Characterization of the Complete Transcriptionally Active *Ehrlichia chaffeensis* 28 kDa Outer Membrane Protein Multigene Family", Gene, 248:59-68 (2000).
McBride et al., "A Conserved, Transcriptionally Action p28 Multigene Locus of *Ehrlichia canis*", Gene, 254:245-252 (2000).
Suksawat et al., "Seroprevalence of *Ehrlichia canis*, *Ehrlichia Equi*, and *Ehrlichia risticii*, in Sick Dogs from North Carolina and Virginia", Journal of Vet. Internal. Med., 14:50-55 (2000).
Waner et al., "Comparison of a clinic-based ELISA test kit with the immunofluorescence test for thie assay of *Ehrlichia canis* antibodies in dogs", J. Vet. Diagn. Invest., 12:240-244 (2000).
Cadman et al., "Comparison of the dot-blot enzyme linked immunoassay with immunofluorescence for detecting antibodies to *Ehrlichia canis*", Veterinary Record, 135:362 (1994).
Zhi et al., "Cloning and expression of the 44-kilodalton major outer membrane protein gene of the human granulocytic ehrlichiosis agent and application of the recombinant protein to serodiagnosis", Journal of Clinical Microbiology, 1666-1673 (1993).
Unver et al., "Western and dot blotting analyses of *Ehrlichia chaffeensis* indirect fluorescent-antibody assay-positive and -negative sera by using native and recombinant *E. chaffeensis* and *E. canis* antigens", Journal of Ciinical Microbiology, 3888-3895 (1999).
McBride et al., "Immunodiagnosis of *Ehrlichia canis* infection with recombinant proteins", Journal of Clinical Microbiology, 39:315-322 (2001).
Reddy et al., "Molecular Characterization of a 28 kDa Surface Antigen Gene Family of the Tribe Ehrlichiae", Biochemical and Biophysical Research Communications, 247:636-643 (1998).
O'Connor et al., "Comparison of an indirect immunofluorescence assay, western blot analysis, and commercially available ELISA for detection of *Ehrlichia canis* antibodies in canine sera", AJVR, 67(2)106-210 (2006).
U.S. Appl. No. 60/335,367, filed Oct. 31, 2001.
O'Connor, "Dogs Vaccinated with Common Lyme Disease Vaccines do not Respond to IR6, the Conserved Immunodominant Region of the VlsE Surface Protein of *Borrelia burgdorferi*", Clinical and Diagnostic, Laboratory Immunology, 458-162 (2004).
Harrus et al., "Comparison of three enzyme-linked irnmunosorbant assays with the indirect immunofluorescent antibody test for the diagnosis of canine infection with *Ehrlichia canis*", Veterinary Microbiology, 86:361-368 (2002).
Kohler et al., "Continuous cultures of Fused Cells Secreting Antibody of Predefined Specificity", Nature, 256:495-497 (1975).
Bowie et al, "Deciphering the Message in Protein Sequences: Tolerance to Amino Acid Substitutions", Science, 247:1306-1310 (1990).
Cunningham et al., "High-Resolution Epitope Mapping of hGH-Receptor Interactions by Alanine-Screening Mutagenesis", Science, 244:1081-1085 (1989).
Wright et al., "Genetically Engineered Antibodies: Progress and Prospects", Critical Reviews in immunology, 12 (3,4):125-168 (1992).
Morrison, "In Vitro Antibodies: Strategies for Production and Application", Annu. Rev. Immunol., 10:239-65 (1992).

Dean, "Preparation and Testing of Monoclonal Antibodies Recombinant Proteins", Methods in Molecular Biology, 80:23-37 (1994).
Dean, "Preparation and characterization of Monoclonal Antibodies to Proteins and Other Cellular Components", Methods in Molecular Biology, 32-361-379 (1994).
Bailey, "The Raising of a Polyclonal Antiserum to a Protein", Methods in Molecular Biology, 32:381-388 (1994).
Gullick, "Production of Antisera to Synthetic Peptides", Methods in Molecular Biology, 32:389-399 (1994).
GenBank Accession No. Q6W715, dated Oct. 31, 2006.
Yabsley et al., "Molecular Variation in the Variabie-Length PCR Target and 120-Kilodalton Antigen Genes of *Ehrlichia chaffeensis* from White-Tailed Deer (*Odocoileus virginianus*)", Journal of Clinical Microbiology, 41(11):5202-5206 (2003).
U.S. Appl. No. 12/234,305, filed Sep. 19, 2008.
Tam, "Recent advances in multiple antigen peptides", Journal of Immunological Methods, 196:17-32 (1996).
Greenspan et al., "Defining epitopes: It's not as easy as it seems", Nature Biotechnology, 17:936-937 (1999).
McGuinness et al., "Point mutation in menigococcal por A gene associated with increased endemic disease", The Lancet, 337:514-517 (1991).
McGuinness et al., "Class 1 outer membrane protein of *Neisseria meningitidis*: epitope analysis of the antigenic diversity between strains, implications for subtype definition and molecular epidemiology", Molecular Microbiology, 7 (4):505-514 (1993).
International Search Report for corresponding application PCT/US08/77079 dated Mar. 3, 2009.
Sumner et al., "Molecular Cloning and Characterization of the *Ehrlichia chaffeensis* Variable Length PCR Target: an Antigen-Expressing Gene That Exhibits Interstrain Variation", Journal of Clinical Microbiology, 37(5):1447-1453 (1999).
International Search Report for corresponding application PCT/US08/77078 dated May 6, 2009.
Cheng et al., "Molecular Heterogeneity of *Ehrlichia chaffeensis* Isolates Determined by Sequence Analysis of the 28-Kilodalton Outer Membrane Protein Genes and other Regions of the Genome", Infection and Immunity, 71(1)-187-195 (2003).
Yu et al., "Cloning and sequencing of the gene for a 120-kDa immunodominant protein of *Ehrlichia chaffeensis*" Gene, 184:149-154 (1997).
Ohashi et al., "Characterization and Trascriptional Analysis of Gene Clusters for a Type IV Secretion Machinery in Human Granulocytic and Monocytic Ehrlichiosis Agents", Infection and Immunity, 70(4):2128-2138 (2002).
Office action dated Jul. 6, 2009, for U.S. Appl. No. 12/234,105, filed Sep. 19, 2008.
Yu et al,, "The Recombinant 120-Kilodalton Protein of *Ehrlichia chaffeensis*, a Potential Diagnostic Tool", Journal of Clinical Microbiology, 34(11):2853-2855 (1996).
Yu et al., "Molecular Cloning and Characterization of the 120-Kilodalton Protein Gene of *Ehrlichia canis* and Application of the Recombinant 120-Kilodalton Protein for Serodiagnosis of Canine Ehrlichiosis", Journal of Clinical Microbiology, 38(1):369-374 (2000).
Bzymek, et al., "Instability of repetitive DNA sequences: the role of replication in multiple mechanisms", Proc. Natl. Acad. Sci. USA, 98:8319-8325 (2001).
Chen, et al., "Analysis and ultrastructural localization of *Ehrlichia chaffeensis* proteins with monoclonal antibodies", Am. J. Trop. Med. Hyg., 54:405-412 (1996).
Chen, et al. "Genetic and antigenic diversity of *Ehrlichia chaffeensis*: comparative analysis of a novel human strain from Oklahoma and previously isolated strains", J. Infect. Dis., 175(4):856-863 (1997).
Collins, et al., "the genome of the heartwater agent *Ehrlichia ruminantium* contains multiple tandem repeats of actively variable copy number", Proc. Natl. Acad. Sci. USA, 102:838-843 (2005).
Doyle, et al., "Differentially expressed and secreted major immunoreactive protein orthologs of *Ehrlichia canis* and *E. chaffeensis* elicit early antibody responses to epitopes on glycosylated tandem repeats", Infect Immun., 74:711-720 (2006).

Doyle, et al., "Molecular characterization of *E. canis* gp36 and *E. chaffeensis* gp47 tandem repeats among different geographic locations", An.. N.Y. Acad. Sci., 1063 (2006).

Dunning Hotopp et al., "Comparative genomics of emerging human ehrlichiosis agents", PLoS Gent., 2:e21 (2006).

Frutos, et al., "Comparaative genomic analysis of three strains of *Ehrlichia ruminantium* reveals an active process of genome size plasticity", J. Bacteriol., 188:2533-2542 (2006).

Garcia-Ortega, et al., "Anomalous electrophoretic behavior of a very acidic protein: ribonuclease U2", Electrophoresis, 26:3407-3413 (2005).

Graceffa et al., "Modification of acidic residues normalizes sodium dodecyl sulfate-polyacrylamide gel electrophoresis of caldesmon and other proteins that migrate anomalously", Arch. Biochem. Biophys., 297:46-51 (1992).

Lin, "*Anaplasma phagocytophilum* AnkA secreted by type IV secretion system is tyrosine phosphorylated by Abl-1 to facilitate infection", Cell Microbiol., 9:2644-2657 (2007).

Luo, et al., "A variable-length PCR target protein of *Ehrlichia chaffeensis* contains major species-specific antibody eptiopes in acidic serine-rich tandem repeats", Infection and Immunity, 76(4):1572-1580 (2008).

Mavromatis, et al., "The genome of the obligately intracellular bacterium *Ehrlichia canis* reveals themes of complex membrane structure and immune evasion strategies", J. Bacteriol., 188:4015-4023 (2006).

McBride, et al., "Glycosylation of homologous immunodominant proteins of *Ehrlichia chaffeensis* and *E. canis*", Infect. Immun., 68:13-18 (2000).

McBride, et al., "Identification of a glycosylated *Ehrlichia canis* 19-kilodalton major immunoreactive protein with a species-specific serine-rich glycopeptide epitope", Infection and Immunity, 75(1):74-82 (2007).

McBride, et al., "Kinetics of antibody response to *Ehrlichia canis* immunoreactive proteins", Infect. Immun., 71:2516-2524 (2003).

McBride, et al., "Novel immunoreactive glycoprotein orthologs of *Ehrlcihia* supp", Ann. N.Y. Acad. Sci., 990:678-684 (2003).

McBride, et al., "PCR detection of acute *Ehrlichia canis* infection in dogs", J. Vet. Diagn. Invest, 8:441-447 (1996).

Moussa, et al., "Abnormal migration of human wild-type alpha-synuclein upon gel electrophoresis", Neurosci. Lett., 371 (2-3):239-43 (2004).

Munodzana, et al., "Conformational dependence of *Anaplasma marginale* major surface protein 5 surface-exposed B-cell epitopes", Infection & Immunity, 66:2619-2624 (1998).

Nethery, et al., "*Ehrlichia canis* gp200 contains dominant species-specific antibody epitopes in terminal acidic domains", Infect. Immun., 75:4900-4908 (2007).

PCT International Search Report and Written Opinion, issued in International application No. PCT/US2009/030527, mailed Sep. 22, 2009.

Popov, et al., "The 120-kDa outer membrane protein of *Ehrlichia chaffeensis*: preferential expression on dense-core cells and gene expression in *Escherichia coli* associated with attachment and entry", Microb. Path. 28:71-80 (2000).

Rikihisa, et al., "Analyses of *Ehrlichia canis* and a canine granulocytic *Ehrlichia* infection", J. Clin. Microbiol., 30:143-148 (1992).

Signu, et al., "*Ehrlichia chaffeensis* expresses macrophage- and tick cell-specific 28-kilodalton outer membrane proteins", Infect. Immun., 73:79-87 (2005).

Yu, et al., "Short report: geographic distribution of different genetic types of *Ehrlichia chaffeensis*", Am. J. Trop. Med. Hyg., 56:679-680 (1997).

Zhu, et al., "Nuclear translocated *Ehrlichia chaffeensis* ankyrin protein interacts with a specific adenine-rich motif of host promoter and intronic Alu elements", Infect. Immun., 77:4243-4255 (2009).

US 8,409,817 B2

METHODS AND COMPOSITIONS FOR DETECTION OF *EHRLICHIA CHAFFEENSIS* (VLPT)

PRIORITY

This application is a divisional of U.S. Ser. No. 12/234,188 (now allowed), filed Sep. 19, 2008, which claims the benefit of U.S. Ser. No. 60/974,196, filed on Sep. 21, 2007. These applications are incorporated herein by reference in their entirety.

SEQUENCE LISTING

This document incorporates by reference an electronic sequence listing text file, which was electronically submitted along with this document. The text file is named "07885US ST25.txt", is 5,000 bytes, and was created on Jun. 16, 2011.

BACKGROUND OF THE INVENTION

The *Ehrlichia* are obligate intracellular pathogens that infect circulating lymphocytes in mammalian hosts. *Ehrlichia canis* and *Ehrlichia chaffeensis* are members of the same sub-genus group that infect canines and humans and can each cause canine monocytic ehrlichiosis (CME) and human monocytic ehrlichiosis (HME), respectively. The canine disease is characterized by fever, lymphadenopathy, weight loss, and pancytopenia. In humans the disease is characterized by fever, headache, mylagia, and leukopenia. Early detection and treatment are important for treating both canine and human ehrlichiosis.

Indirect immunofluorescense assays (IFA) and enzyme-linked immunosorbent assays (ELISA) are frequently used as aids in the diagnosis of these diseases. These assays measure or otherwise detect the binding of anti-*Ehrlichia* antibodies from a patient's blood, plasma, or serum to infected cells, cell lysates, or purified *Ehrlichia* proteins. However, many assays for detecting anti-*Ehrlichia chaffeensis* antibodies or fragments thereof are severely limited in usefulness because of sensitivity and specificity issues directly related to the impure nature of the *Ehrlichia* antigen used in these tests. Additionally, animals vaccinated for *E. canis* may show a positive result when tested for *E. chaffeensis* due to immunological cross-reaction. Highly purified, specific reagents are needed to construct more accurate assays.

SUMMARY OF THE INVENTION

One embodiment of the invention provides a purified polypeptide comprising SEQ ID NO:3, wherein the polypeptide consists of less than about 50 contiguous naturally occurring *Ehrlichia chaffeensis* amino acids; SEQ ID NO:2, wherein the polypeptide consists of less than about 50 contiguous naturally occurring *Ehrlichia chaffeensis* amino acids; SEQ ID NO:1, wherein the polypeptide consists of less than about 50 contiguous naturally occurring *Ehrlichia chaffeensis* amino acids. The purified polypeptides can consist of SEQ ID NO:3, SEQ ID NO:2, or SEQ ID NO:1. The invention also provides isolated polynucleotides that encode the purified polypeptide of the invention.

A purified polypeptide of the invention can be linked to an indicator reagent, an amino acid spacer, an amino acid linker, a signal sequence, a stop transfer sequence, a transmembrane domain, a protein purification ligand, a heterologous polypeptide, one or more additional polypeptides comprising SEQ ID NOs:1, 2, 3, 4, 5, 6, or a combination thereof. A purified polypeptide of the invention can comprise one or more C amino acid residues at the amino terminus or carboxy terminus or both termini of the polypeptide.

Another embodiment of the invention provides a method of detecting antibodies that specifically bind an *Ehrlichia chaffeensis* polypeptide in a test sample. The method comprises contacting a purified polypeptide comprising SEQ ID NO:1, 2, 3, 5, or 6, with the test sample, under conditions that allow polypeptide/antibody complexes to form; wherein the purified polypeptide consists of less than about 50 contiguous naturally occurring *Ehrlichia chaffeensis* amino acids; and detecting the polypeptide/antibody complexes. The detection of the polypeptide/antibody complexes is an indication that antibodies specific for *Ehrlichia chaffeensis* are present in the test sample, and the absence of the polypeptide/antibody complexes is an indication that antibodies specific for *Ehrlichia chaffeensis* are not present in the test sample. The complexes can be contacted with an indicator reagent prior to the performance of the detecting step. In one embodiment of the invention, the purified polypeptide is SEQ ID NOs:1-3, 5 or 6 and the method does not detect antibodies that specifically bind an *Ehrlichia canis* polypeptide. The amount of antibody in the test sample can be determined. The purified polypeptide can be attached to a substrate. The purified polypeptide can be linked to an indicator reagent, an amino acid spacer, an amino acid linker, a signal sequence, a stop transfer sequence, a transmembrane domain, a protein purification ligand, a heterologous protein, one or more additional polypeptides comprising SEQ ID NOs:1, 2, 3, 4, 5, or 6, or a combination thereof.

Even another embodiment of the invention provides a method of detecting an *Ehrlichia chaffeensis* infection in a subject. The method comprises obtaining a biological sample from the subject; contacting a purified polypeptide comprising SEQ ID NO:1, 2, 3, 5, or 6 with the biological sample under conditions that allow polypeptide/antibody complexes to form; wherein the purified polypeptide consists of less than about 50 contiguous naturally occurring *Ehrlichia chaffeensis* amino acids; and detecting the polypeptide/antibody complexes. The detection of the polypeptide/antibody complexes is an indication that the subject has an *Ehrlichia chaffeensis* infection and the absence of the polypeptide/antibody complexes is an indication that the subject does not have an *Ehrlichia chaffeensis* infection. In one embodiment of the invention, the purified polypeptide is SEQ ID NOs:1, 2, 3, 5, or 6 and the method does not detect *Ehrlichia canis* infection in the subject.

Another embodiment of the invention provides an antibody that specifically binds to a polypeptide consisting of SEQ ID NO:1, 2, 3, 5, or 6. The antibody can be a monoclonal antibody, polyclonal antibody, antigen-binding antibody fragment, or a single chain antibody.

Yet another embodiment of the invention provides a method of detecting an *Ehrlichia chaffeensis* polypeptide in a sample. The method comprises contacting antibodies that specifically bind to a polypeptide consisting of SEQ ID NO:1, 2, 3, 5, or 6 with the sample under conditions that allow polypeptide/antibody complexes to form; and detecting the polypeptide/antibody complexes. The detection of the polypeptide/antibody complexes is an indication that an *Ehrlichia chaffeensis* polypeptide is present in the sample and the absence of the polypeptide/antibody complexes is an indication that an *Ehrlichia chaffeensis* polypeptide is not present in the sample. In one embodiment of the invention the purified polypeptide can be SEQ ID NOs:1, 2, 3, 5, or 6 and the method does not detect an *Ehrlichia* polypeptide in the sample. The antibodies can be monoclonal antibodies, polyclonal antibodies, antigen-binding antibody fragments, or single chain antibodies. The antibodies can be attached to a substrate.

Therefore, the invention provides compositions and methods for the detection of *E. chaffeensis*.

DETAILED DESCRIPTION OF THE INVENTION

*Ehrlichia chaffeensis* Polypeptides

Figure 1A:
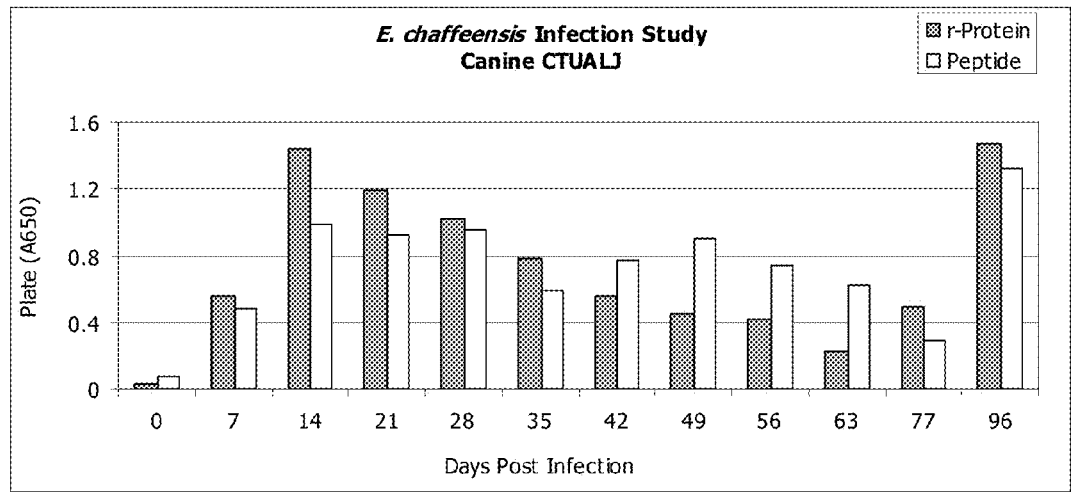
FIGS. 1A and 1B show the results of serum assays of dogs that were experimentally infected with *E. chaffeensis*. VLPT-1 (SEQ ID NO:5) (shown as "Peptide" in the figures) and VLPT-R (SEQ ID NO:4 where the X at position 112 is P) (shown as "r-Protein" in the figures) both were able to detect *E. chaffeensis* antibodies by day 7 post-infection.

As used herein, the singular forms "a," "an", and "the" include plural referents unless the context clearly dictates otherwise.

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

One embodiment of the invention provides a purified *Ehrlichia chaffeensis* polypeptide as shown in SEQ ID NO: 1, SEQ ID NO:2, SEQ ID NO:3, SEQ ID NO:4, SEQ ID NO:5 or SEQ ID NO:6.

```
XSDLHXXXXVELXXPSKEEVQXEXDXXXXXX    SEQ ID NO: 1

DSDLHGXFSVELFDPSKEEVQLESDLQQSSN    SEQ ID NO: 2

NSDLHEXSFVELPGPSKEEVQFEDDAKNVVY    SEQ ID NO: 3
```

For all sequences, an X can stand for any amino acid. In one embodiment of the invention, in SEQ ID NO:1 the X at position 1 is D or N, the X at position 6 is G or E, the X at position 7 is P or S, the X at position 8 is F or S, the X at position 9 is S or F, the X at position 13 is F or P, the X at position 14 is D or G, the X at position 22 is L or F, the X at position 24 is S or D, the X at position 26 is L or A, the X at position 27 is Q or K, the X at position 28 is Q or N, the X at position 29 is S or V, the X at position 30 is S or V, the X at position 31 is N or Y. For SEQ ID NOs: 2 and 3, the X at position 7 can be P or S. Each of SEQ ID NOs:1-3 may have an N-terminal C residue. Alternatively, the N-terminal C residue can be absent. Polypeptide VLPT-1 is SEQ ID NO:2 with an amino terminal C residue (i.e., CDSDLHGPFS-VELFDPSKEEVQLESDLQQSSN; SEQ ID NO:5). Polypeptide VLPT-2 is SEQ ID NO:3 with an amino terminal C residue (i.e., CNSDLHESSFVELPGPSKEEVQFED-DAKNVVY; SEQ ID NO:6).

Another embodiment of the invention comprises a purified polypeptide comprising SEQ ID NO:4:

```
MSQFSEDNIG NIQMPFSNLQ ESSHLELPSL SEKVIHLESG LQQSSDSDSH EPSHLELPSL    60

SEEVIQLESD LQQSSNSDLH GSFSVELFDP FKEAVQLGND LQQSSDSDLH GXFSVELFDP   120

SKEEVQLESD LQQSSNSDLH ESSFVELPGP SKEEVQFEDD AKNVVYGQDH VSLSELG      177
```

The X at position 112 can be P or S.

One embodiment provides a purified polypeptide comprising SEQ ID NO:1-6, wherein the polypeptide consists of less than about 175, 150, 125, 100, 90, 80, 70, 60, 50, 40, 35. 34, 33, 32, or 31 (or any range between about 31 and about 175) contiguous naturally occurring *Ehrlichia chaffeensis* amino acids. In one embodiment of the invention a purified polypeptide consists of more than about 31, 32, 33, 34, 35, 40, 50, 60, 70, 80, 90, 100, 125, 150, or 175 (or any range between about 31 and about 175) contiguous naturally occurring *Ehrlichia chaffeensis* amino acids (i.e, the purified polypeptide does not encompass the entire naturally occurring *Ehrlichia chaffeensis* VLPT polypeptide). Naturally occurring *Ehrlichia chaffeensis* amino acids are any polypeptides naturally produced by an *Ehrlichia chaffeensis* organism. That is, a purified polypeptide comprises a polypeptide shown in SEQ ID NOs: 1-6 but consists of less than about 175, 150, 125, 100, 90, 80, 70, 60, 50, 40, or 35 contiguous naturally occurring *Ehrlichia chaffeensis* amino acids.

The fact that polypeptides SEQ ID NOs:1-3 and 5-6 are smaller than the full length *Ehrlichia chaffeensis* polypeptide VPLT is important because smaller polypeptides can have greater specificity and/or sensitivity than full length polypeptides assays. Additionally, these smaller polypeptides can be less expensive to manufacture, and may be obtained at greater purity than the full length polypeptide.

One embodiment of the invention provides a purified polypeptide that is less than about 175, 150, 125, 100, 90, 80, 70, 60, 50, 40, or 35 contiguous naturally *Ehrlichia chaffeensis* amino acids and greater than about 10, 20, 25, or 30, contiguous amino acids of SEQ ID NOs:1-6.

One embodiment of the invention provides a purified polypeptide comprising at least about 10, 20, 25, 30, 35, 40, 50 or more contiguous amino acids of SEQ ID NOs:1-6. Therefore, a polypeptide of the invention can be, for example, about 35 to about 40; about 35 to about 50; about 35 to about 100; or about 35 to about 150 amino acids in length. In one embodiment of the invention, the polypeptide comprises from about amino acid residue 120 to about amino acid residue 177 of SEQ ID NO:4; from about amino acid residue 130 to about amino acid residue 170 of SEQ ID NO:4; or from about amino acid residue 135 to about 168 of SEQ ID NO:4.

Variant polypeptides are at least about 80%, or about 81, 82, 83, 84, 85, 86, 87, 88, 89, 90, 91, 92, 93, 94, 95, 96, 97, 98, or 99% identical to the polypeptide sequences shown in SEQ ID NOs:1-6 and are also polypeptides of the invention. For example, a variant polypeptide of SEQ ID NOs:1-3 can be about at least 97% (about 1 amino acid change), 94% (about 2 amino acid changes), 90% (about 3 amino acid changes), 87% (about 4 amino acid changes), 84% (about 5 amino acid changes), or 81% (about 6 amino acid changes) identical to SEQ ID NOs:1-3. A variant polypeptide of SEQ ID NOs:5-6 can be about at least 97% (about 1 amino acid change), 94% (about 2 amino acid changes), 91% (about 3 amino acid changes), 88% (about 4 amino acid changes), 84% (about 5 amino acid changes), or 81% (about 6 amino acid changes) identical to SEQ ID NOs:5-6. Variant polypeptides have one or more conservative amino acid variations or other minor modifications and retain biological activity, i.e., are biologically functional equivalents. A biologically active equivalent has substantially equivalent function when compared to the corresponding wild-type polypeptide. In one embodiment of the invention a polypeptide has about 1, 2, 3, 4, 5, 10, 20, 30, 40, 50 or less conservative amino acid substitutions.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variant polypeptides can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a non-*Ehrlichia chaffeensis* organism, a synthetic sequence, or an *Ehrlichia chaffeensis* sequence not usually located at the carboxy or amino terminus of a polypeptide of the invention. Additionally, a polypeptide can be covalently or non-covalently linked to compounds or molecules other than amino acids, such as indicator reagents. A polypeptide can be covalently or non-covalently linked to an amino acid spacer, an amino acid linker, a signal sequence, a stop transfer sequence, a transmembrane domain, a protein purification ligand, or a combination thereof. A polypeptide can also be linked to a moiety (i.e., a functional group that can be a polypeptide or other compound) that enhances an immune response (e.g., cytokines such as IL-2), a moiety that facilitates purification (e.g., affinity tags such as a six-histidine tag, trpE, glutathione, maltose binding protein), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more C amino acid residues at, for example, the amino terminus or carboxy terminus or both termini of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a polypeptide of the invention can be part of a fusion protein, which contains other amino acid sequences, such as amino acid linkers, amino acid spacers, signal sequences, TMR stop transfer sequences, transmembrane domains, as well as ligands useful in protein purification, such as glutathione-S-transferase, histidine tag, and *Staphylococcal* protein A. More than one polypeptide of the invention can be present in a fusion protein of the invention. A polypeptide of the invention can be operably linked to non-*Ehrlichia chaffeensis* proteins or non-*Ehrlichia chaffeensis* VLPT proteins to form fusion proteins. A fusion protein of the invention can comprise one or more of *Ehrlichia chaffeensis* polypeptides of the invention, fragments thereof, or combinations thereof. A fusion protein does not occur in nature. The term "operably linked" means that the polypeptide of the invention and the other polypeptides are fused in-frame to each other either to the N-terminus or C-terminus of the polypeptide of the invention.

Polypeptides of the invention can be in a multimeric form. That is, a polypeptide can comprise one or more copies of an *Ehrlichia chaffeensis* polypeptide of the invention or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody specific for *Ehrlichia chaffeensis*. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span an entire polypeptide sequence, can be prepared by proteolytic cleavage. By starting with, for example, 30-mer polypeptide fragments (or smaller fragments), each fragment can be tested for the presence of epitopes recognized in an ELISA. For example, in an ELISA assay an *Ehrlichia chaffeensis* polypeptide, such as a 30-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 30-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *Ehrlichia chaffeensis* cells.

An immunogenic polypeptide of the invention can comprise an amino acid sequence shown in SEQ ID NOs:1-6 or fragments thereof. An immunogenic polypeptide can elicit antibodies or other immune responses (e.g., T-cell responses of the immune system) that recognize epitopes of a polypeptide having SEQ ID NOs:1-6. An immunogenic polypeptide of the invention can also be a fragment of a polypeptide that has an amino acid sequence shown in SEQ ID NOs:1-6. An immunogenic polypeptide fragment of the invention can be about 6, 10, 15, 20, 25, 30, 40, 50, 60, 70, 80, 90, 100, 150, 170 (or any range between 6 and 170) or more amino acids in length. An immunogenic polypeptide fragment of the invention can be about 170, 150, 100, 90, 80, 70, 60, 50, 40, 30, 20, 15, 10, 6, or less amino acids in length (or any range between 170 and 6).

*Ehrlichia chaffeensis* Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered an isolated polynucleotide.

The polynucleotides of the invention encode the polypeptides of the invention described above. In one embodiment of the invention the VLPT polynucleotides encode a polypeptide shown in SEQ ID NOs:1-6 or fragments thereof.

Polynucleotides of the invention can consist of less than about 530, 500, 400, 300, 250, 200, 150, 100 or 90 (or any range between 90 and 530) contiguous, naturally occurring *Ehrlichia chaffeensis* polynucleotides. Polynucleotides of the invention can consist of greater than about 90, 100, 150, 200, 250, 300, 400, 500, 530 (or any range between 90 and 530), or more contiguous, naturally occurring *Ehrlichia chaffeensis* polynucleotides. The purified polynucleotides can comprise additional heterologous nucleotides (that is, nucleotides that are not from *Ehrlichia chaffeensis*) and even additional *Ehrlichia chaffeensis* amino acids as long as they do not naturally occur contiguously with *Ehrlichia chaffeensis* VLPT polynucleotides. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and *Staphylococcal* protein A. One embodiment of the invention provides a purified polynucleotide comprising at least about 6, 10, 15, 20, 25, 30, 40, 50, 75, 100, 200, 300, 400, 500, 600, 700, 800, 900, 1,000, or more contiguous nucleotides of encoding SEQ ID NOs:1-6.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *Ehrlichia chaffeensis* polynucleotides that encode biologically functional *Ehrlichia chaffeensis* polypeptides also are *Ehrlichia chaffeensis* polynucleotides.

Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366, 246. A polynucleotide of the invention is operably linked when it is positioned adjacent to or close to one or more expression control elements, which direct transcription and/or translation of the polynucleotide.

Polynucleotides of the invention can be used, for example, as probes or primers, for example, PCR primers, to detect the presence of *Ehrlichia chaffeensis* polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

A probe or primer can be about 10, 15, 20, 25, 30, 40, 50, 60, 70, 80, 90, 100, or more contiguous nucleotides that encode polypeptides shown in SEQ ID NOs:1-6.

The hybridization of nucleic acids is well understood in the art and discussed herein. Typically a probe can be made from any combination of nucleotides or nucleotide derivatives or analogs available in the art. The ability of such probes and primers to specifically hybridize to *Ehrlichia chaffeensis* polynucleotide sequences will enable them to be of use in detecting the presence of complementary sequences in a given test sample. Polynucleotide probes and primers of the invention can hybridize to complementary sequences in a test sample such as a biological sample, including saliva, sputum, blood, plasma, serum, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers, are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of *Ehrlichia chaffeensis* polynucleotide in the sample.

Antibodies

Antibodies of the invention are antibody molecules that specifically bind to an *Ehrlichia chaffeensis* polypeptide of the invention, variant polypeptides of the invention, or fragments thereof. An antibody of the invention can be specific for an *Ehrlichia chaffeensis* polypeptide, for example, an antibody specific for one or more SEQ ID NOs:1-6. In another embodiment of the invention an antibody is specific for an *Ehrlichia chaffeensis* polypeptide and is not specific for an *Ehrlichia canis* polypeptide (e.g., an antibody specific for SEQ ID NOs:1-6). One of skill in the art can easily determine if an antibody is specific for an *Ehrlichia chaffeensis* polypeptide using assays described herein. An antibody of the invention can be a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antigen binding antibody fragments include Fab, Fab', Fab'-SH, $F(ab')_2$ and $F_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds," "specifically bind," or "specific for" means that a first antigen, e.g., an *Ehrlichia chaffeensis* polypeptide, recognizes and binds to an antibody of the invention with greater affinity than to other, non-specific molecules. "Specifically binds," "specifically bind" or "specific for" also means a first antibody, e.g., an antibody raised against SEQ ID NOs:1-6, recognizes and binds to SEQ ID NOs:1-6, with greater affinity than to other non-specific molecules. A non-specific molecule is an antigen that shares no common epitope with the first antigen. In a preferred embodiment of the invention a non-specific molecule is not derived from Ehrlichia sp., and in particular is not derived from Ehrlichia chaffeensis or Ehrlichia canis. "Ehrlichia sp." refers to all species of the genus Ehrlichia. For example, an antibody raised against a first antigen (e.g., a polypeptide) to which it binds more efficiently than to a non-specific antigen can be described as specifically binding to the first antigen. In one embodiment, an antibody or antigen-binding portion thereof specifically binds to a polypeptide of SEQ ID NOs: 1-6 or fragments thereof when it binds with a binding affinity $K_a$ of $10^7$ l/mol or more. Specific binding can be tested using, for example, an enzyme-linked immunosorbant assay (ELISA), a radioimmunoassay (RIA), or a western blot assay using methodology well known in the art.

Antibodies of the invention include antibodies and antigen binding fragments thereof that (a) compete with a reference antibody for binding to SEQ ID NOs:1-6 or antigen binding fragments thereof; (b) binds to the same epitope of SEQ ID NOs:1-6 or antigen binding fragments thereof as a reference antibody; (c) binds to SEQ ID NOs:1-6 or antigen binding fragments thereof with substantially the same $K_d$ as a reference antibody; and/or (d) binds to SEQ ID NOs:1-6 or fragments thereof with substantially the same off rate as a reference antibody, wherein the reference antibody is an antibody or antigen-binding fragment thereof that specifically binds to a polypeptide of SEQ ID NOs:1-6 or antigen binding fragments thereof with a binding affinity $K_a$ of $10^7$ l/mol or more.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing Ehrlichia-specific antibodies can be identified using RIA or ELISA and isolated by cloning in semi-solid agar or by limiting dilution. Clones producing Ehrlichia-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., P.N.A.S. U.S.A. 82:8653 1985; Spria et al., J. Immunolog. Meth. 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., Nature 321:522 (1986); Reichmann et al., Nature 332:323 (1988); Presta, Curr. Op. Struct. Biol. 2:593 (1992)), caninized, canine, or human antibodies. Human antibodies can be made by, for example, direct immortilization, phage display, transgenic mice, or a Trimera methodology, see e.g., Reisener et al., Trends Biotechnol. 16:242-246 (1998).

Antibodies that specifically bind Ehrlichia chaffeensis are particularly useful for detecting the presence of Ehrlichia chaffeensis antigens in a sample, such as a serum, blood, plasma, cell, tissue, urine, fecal, or saliva sample from an animal. An immunoassay for can utilize one antibody or several antibodies. An immunoassay can use, for example, a monoclonal antibody specific for one epitope, a combination of monoclonal antibodies specific for epitopes of one polypeptide, monoclonal antibodies specific for epitopes of different polypeptides, polyclonal antibodies specific for the same antigen, polyclonal antibodies specific for different antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels. In one embodiment of the invention, antibodies of the invention specifically bind Ehrlichia chaffeensis antigens and do not specifically bind to Ehrlichia canis antigens.

Antibodies of the invention or antigen-binding fragments thereof can be bound to a support and used to detect the presence of Ehrlichia chaffeensis antigens. Supports include, for example, glass, polystyrene, polypropylene, polyethylene, dextran, nylon, amylases, natural and modified celluloses, polyacrylamides, agaroses and magletite.

Antibodies of the invention can further be used to isolate Ehrlichia chaffeensis organisms or antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind Ehrlichia chaffeensis organisms or Ehrlichia chaffeensis antigens from a sample, such as a biological sample including saliva, serum, sputum, blood, urine, feces, cerebrospinal fluid, amniotic fluid, wound exudate, or tissue. The bound Ehrlichia organisms or Ehrlichia antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by Ehrlichia chaffeensis. By measuring the increase or decrease of antibodies specific for Ehrlichia chaffeensis in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection

The methods of the invention can be used to detect antibodies or antigen-binding antibody fragments specific for Ehrlichia chaffeensis antigens or Ehrlichia chaffeensis polynucleotides in a test sample, such as a biological sample, an environmental sample, or a laboratory sample. A test sample can potentially comprise Ehrlichia sp. polynucleotides, Ehrlichia chaffeensis polynucleotides, Ehrlichia canis polynucleotides, *Ehrlichia* sp. polypeptides, *Ehrlichia chaffeensis* polypeptides, *Ehrlichia canis* polypeptides, antibodies specific for *Ehrlichia* sp., antibodies specific for *Ehrlichia chaffeensis*, and/or antibodies specific for *Ehrlichia canis*, unrelated polynucleotide and polypeptides, combinations thereof, or none of the above. A biological sample can include, for example, sera, blood, cells, plasma, saliva, urine, feces, or tissue from a mammal such as a horse, cat, dog or human. The test sample can be untreated, precipitated, fractionated, separated, diluted, concentrated, or purified.

In one embodiment methods of the invention comprise contacting one or more polypeptides of the invention with a test sample under conditions that allow polypeptide/antibody complexes, i.e., immunocomplexes, to form. That is, polypeptides of the invention specifically bind to antibodies specific for *Ehrlichia chaffeensis* antigens located in the sample. In one embodiment of the invention one or more polypeptides of the invention specifically bind to antibodies that are specific for *Ehrlichia chaffeensis* antigens and do not specifically bind to *Ehrlichia canis* antigens. One of skill in the art is familiar with assays and conditions that are used to detect antibody/polypeptide complex binding. The formation of a complex between polypeptides and antibodies in the sample is detected. The formation of antibody/polypeptide complexes is an indication that *Ehrlichia chaffeensis* polypeptides are present in the sample. The lack of detection of the polypeptide/antibody complexes is an indication that *Ehrlichia chaffeensis* polypeptides are not present in the sample.

Antibodies of the invention can be used in a method of the diagnosis of *Ehrlichia chaffeensis* infection by obtaining a test sample from, e.g., a human or animal suspected of having an *Ehrlichia chaffeensis* infection. The test sample is contacted with antibodies of the invention under conditions enabling the formation of antibody-antigen complexes (i.e., immunocomplexes). One of skill in the art is aware of conditions that enable and are appropriate for formation of antigen/antibody complexes. The amount of antibody-antigen complexes can be determined by methodology known in the art. A level that is higher than that formed in a negative control sample indicates an *Ehrlichia chaffeensis* infection. A negative control sample is a sample that does not comprise any *Ehrlichia chaffeensis* and/or *Ehrlichia canis* polypeptides or antibodies specific for *Ehrlichia chaffeensis* and/or *Ehrlichia canis*. In one embodiment of the invention the negative control contains no *Ehrlichia* sp. polypeptides or antibodies specific for *Ehrlichia* sp. In one embodiment of the invention an antibody is specific for *Ehrlichia chaffeensis* antigens and is not specific for *Ehrlichia canis* antigens. Alternatively, a polypeptide of the invention can be contacted with a test sample. Antibodies specific *Ehrlichia chaffeensis* in a positive test sample will form antigen-antibody complexes under suitable conditions. The amount of antibody-antigen complexes can be determined by methods known in the art.

In one embodiment of the invention, *Ehrlichia chaffeensis* infection can be detected in a subject. A biological sample is obtained from the subject. One or more purified polypeptides comprising SEQ ID NOs:1-6 or other polypeptides of the invention are contacted with the biological sample under conditions that allow polypeptide/antibody complexes to form. The polypeptide/antibody complexes are detected. The detection of the polypeptide/antibody complexes is an indication that the mammal has an *Ehrlichia chaffeensis* infection. The lack of detection of the polypeptide/antibody complexes is an indication that the mammal does not have an *Ehrlichia chaffeensis* infection.

In one embodiment of the invention, *Ehrlichia chaffeensis* infection can be detected in a subject by about 5 days, 6 days, 7 days, 8 days, 9 days, 10 days, 11 days, 12 days, 13 days, 14 days, 15 days, 16 days, 17 days, 18 days, 19 days, 20 days, 21 days or more after the subject acquired the *Ehrlichia chaffeensis* infection. In one embodiment of the invention, *Ehrlichia chaffeensis* infection can be detected in a subject by about 21 days, 20 days, 19 days, 18 days, 17 days, 16 days, 15 days, 14 days, 13 days, 12 days, 11 days, 10 days, 9 days, 8 days, 7 days, 6 days, 5 days, or less after the subject acquired the *Ehrlichia chaffeensis* infection.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, one or more antibodies of the invention are attached to a solid phase or substrate. A test sample potentially comprising a protein comprising a polypeptide of the invention is added to the substrate. One or more antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, one or more antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise and indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay. See e.g., U.S. Pat. No. 5,726,010.

Assays can use solid phases or substrates or can be performed by immunoprecipitation or any other methods that do not utilize solid phases. Where a solid phase or substrate is used, one or more polypeptides of the invention are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment of the invention a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing anti-*Ehrlichia chaffeensis* antibodies or antigen-binding fragments thereof is incubated with an indicator reagent comprising a signal generating compound conjugated to an antibodies or antibody fragments specific for *Ehrlichia chaffeensis* for a time and under conditions sufficient to form antigen/antibody complexes of either antibodies of the test sample to the polypeptides of the solid phase or the indicator reagent compound conjugated to an antibody specific for *Ehrlichia chaffeensis* to the polypeptides of the solid phase. The reduction in binding of the indicator reagent conjugated to anti-*Ehrlichia chaffeensis* antibodies to the solid phase can be quantitatively measured. A measurable reduction in the signal compared to the signal generated from, e.g., a confirmed negative *Ehrlichia chaffeensis* test sample indicates the presence of anti-*Ehrlichia chaffeensis* antibodies in the test sample. This type of assay can quantitate the amount of anti-*Ehrlichia chaffeensis* antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If antibodies specific for *Ehrlichia chaffeensis* are present in the test sample they will bind the one or more polypeptides conjugated to an indicator reagent and to the one or more polypeptides immobilized on the support. The polypeptide/antibody/indicator complex can then be detected. This type of assay can quantitate the amount of anti-*Ehrlichia chaffeensis* antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If *Ehrlichia chaffeensis* specific antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-*Ehrlichia chaffeensis* antibodies in a test sample.

The formation of a polypeptide/antibody complex or a polypeptide/antibody/indicator complex can be detected by, for example, radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-*Ehrlichia chaffeensis* antibodies in a test sample. Therefore, the methods of the invention can be used to diagnose *Ehrlichia chaffeensis* infection in an animal.

The methods of the invention can also indicate the amount or quantity of anti-anti-*Ehrlichia chaffeensis* antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrated specimens such as urine, in order to determine the presence and/or amount of antibody present.

The invention further comprises assay kits (e.g., articles of manufacture) for detecting anti-*Ehrlichia chaffeensis* antibodies or antigen-binding antibody fragments, or *Ehrlichia chaffeensis* polypeptides in a sample. A kit comprises one or more polypeptides of the invention and means for determining binding of the polypeptide to anti-*Ehrlichia chaffeensis* antibodies or antibody fragments in the sample. A kit or article of manufacture can also comprise one or more antibodies or antibody fragments of the invention and means for determining binding of the antibodies or antibody fragments to *Ehrlichia chaffeensis* polypeptides in the sample. A kit can comprise a device containing one or more polypeptides or antibodies of the invention and instructions for use of the one or more polypeptides or antibodies for, e.g., the identification of an *Ehrlichia chaffeensis* infection in a mammal. The kit can also comprise packaging material comprising a label that indicates that the one or more polypeptides or antibodies of the kit can be used for the identification of *Ehrlichia chaffeensis* infection. Other components such as buffers, controls, and the like, known to those of ordinary skill in art, can be included in such test kits. The polypeptides, antibodies, assays, and kits of the invention are useful, for example, in the diagnosis of individual cases of *Ehrlichia chaffeensis* infection in a patient, as well as epidemiological studies of *Ehrlichia chaffeensis* outbreaks.

Polypeptides and assays of the invention can be combined with other polypeptides or assays to detect the presence of *Ehrlichia chaffeensis* along with other organisms. For example, polypeptides and assays of the invention can be combined with reagents that detect heartworm and/or *Borrelia burgdorferi* and/or *Ehrlichia canis* and/or *Anaplasma platys* and/or *Anaplasma phagocytophilum*.

Polynucleotides of the invention can be used to detect the presence of *Ehrlichia chaffeensis* polynucleotides in a sample. The polynucleotides can be used to detect *Ehrlichia chaffeensis* polynucleotides in a sample by a simple hybridization reaction and can also be used in, e.g., polymerase chain reactions (PCR) such as a real-time PCR reaction.

Methods and compositions of the invention can also be used to differentially detect the presence *Ehrlichia chaffeensis* from other *Ehrlichia* sp., such as *Ehrlichia canis*.

PCR assays are well described in the art, including, for example, U.S. Pat. Nos. 4,683,195; U.S. Pat. No. 4,683,202; U.S. Pat. No. 4,965,188. Generally, polynucleotide primers are annealed to denatured strands of a target nucleic acid. Primer extension products are formed by polymerization of deoxynucleoside triphosphates by a polymerase. PCR then involves repetitive cycles of template nucleic acid denaturation, primer annealing and extension of the annealed primers by the action of a thermostable polymerase. The process results in exponential amplification of the target *Ehrlichia chaffeensis* nucleic acids in the test sample, which allows for the detection of target polynucleotides existing in very low concentrations in a sample.

Real-time PCR assays are based on the detection of a signal, e.g., a fluorescent reporter signal. This signal increases in direct proportion to the amount of PCR product in a reaction. Real-time PCR is any amplification technique that makes it possible to monitor the evolution of an ongoing amplification reaction. See, Quantitation of DNA/RNA Using Real-Time PCR Detection, Perkin Elmer Applied Biosystems (1999); PCR Protocols (Academic Press New York, 1989). By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

One embodiment of the invention provides a method for detecting and/or quantifying *Ehrlichia chaffeensis* polynucleotides in a test sample. Sense primers and antisense primers can be added to a test sample under conditions suitable for a polymerase chain reaction. The primers hybridize with *Ehrlichia chaffeensis* polynucleotides such that an amplification product is formed if *Ehrlichia chaffeensis* polynucleotides are present in the test sample. Amplification products are detected and the presence and/or quantity of *Ehrlichia chaffeensis* polynucleotides is determined. Amplification products can be detected with a polynucleotide probe that hybridizes, under conditions suitable for a polymerase chain reaction, with an *Ehrlichia chaffeensis* polynucleotide sequence. The amplification product can be quantified by measuring a detection signal from the probe and comparing said detection signal to a second probe detection signal from a quantification standard. The quantification standard can be extracted in parallel with the test sample.

Methods of Treatment, Amelioration, or Prevention of a Disease Caused by *E. chaffeensis*

Polypeptides, polynucleotides, and antibodies of the invention can be used to treat, ameliorate, or prevent a disease caused by *E. chaffeensis*.

For example, an antibody, such as a monoclonal antibody of the invention or antigen-binding fragments thereof, can be administered to an animal, such as a human or dog. In one embodiment of the invention an antibody or antigen-binding fragment thereof is administered to an animal in a pharmaceutical composition comprising a pharmaceutically acceptable carrier. A pharmaceutical composition comprises a therapeutically effective amount of an antibody or antigen-binding fragments thereof. A therapeutically effective amount is an amount effective in alleviating the symptoms of an *E. chaffeensis* infection or in reducing the amount of *E. chaffeensis* organisms in a subject.

Polypeptides or polynucleotides of the invention can be present in an immunogenic composition and used to elicit an immune response in a host. An immunogenic composition or immunogen is capable of inducing an immune response in an animal. An immunogenic polypeptide or polynucleotide composition of the invention is particularly useful in sensitizing an immune system of an animal such that, as one result, an immune response is produced that ameliorates or prevents the effect of *E. chaffeensis* infection. The elicitation of an immune response in animal model can be useful to determine, for example, optimal doses or administration routes. Elicitation of an immune response can also be used to treat, prevent, or ameliorate a disease or infection caused by *E. chaffeensis*. An immune response includes humoral immune responses or cell mediated immune responses, or a combination thereof. An immune response can also comprise the promotion of a generalized host response, e.g., by promoting the production of defensins.

One embodiment of the invention provides an immunogen that comprises a polypeptide of the invention and one or more additional regions or moieties covalently joined to the polypeptide at the carboxyl terminus or amino terminus. Each region or moiety can, for example, enhance the immune response, facilitate purification of the immunogen, or facilitate polypeptide stability.

The generation of an antibody titer by an animal against *E. chaffeensis* can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to *E. chaffeensis* can be identified by eliciting antibodies directed against *E. chaffeensis* polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents and veterinarily acceptable carries and diluents for therapeutic use are well known in the art and are described in, for example, Remington's Pharmaceutical Sciences, Mack Publishing Co. (A.R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. Alk(SO$_4$)$_2$; AlNa(SO$_4$)$_2$, AlNH$_4$(SO$_4$), Silica, Alum, Al(OH)$_3$, and Ca$_3$(PO$_4$)$_2$), polynucleotides (i.e. Poly IC and Poly AU acids), and certain natural substances (e.g. wax D from *Mycobacterium tuberculosis*, as well as substances found in *Corynebacterium parvum, Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® 80 (polysorbate) emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with *E. chaffeensis* or can be administered to an *E. chaffeensis*-infected animal. An immunologically effective amount or therapeutically effective amount means the administration of that amount to an individual, either in a single dose or as part of series, is effective for treatment, amelioration, or prevention of *E. chaffeensis* infection. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Direct ELISA Assay Plates and Protocols

Polypeptides shown in SEQ ID NOs:5 and 6 were conjugated to BSA and the conjugate was coated onto IMMULON® 4 plates. The coating buffer was 0.05M sodium carbonate, pH 9.6. 100 uL/well of diluted polypeptide was pipetted onto the plates. The plates were covered and incubated overnight at 2° C.-8° C. The polypeptide solution was aspirated from the plates and the plates were washed 4× with HW PetChek® wash buffer (IDEXX Laboratories, Inc., Westbrook Me.). 300 uL/well of 1% BSA in 0.1M Tris pH 7.6 was added to the plates. The plates were incubated, covered, for 6 hours at RT. The BSA was aspirated and 300 uL/well of 2.5% sucrose in 0.1M Tris pH 7.6 was added to the plates. The plates were incubated, covered, overnight at 2° C.-8° C. The sucrose was aspirated from the plates and the plates were tapped to remove excess liquid. The plates were dried in a vacuum chamber for 4 hours. The plates were stored with desiccants in double plastic bags at 2° C.-8° C.

Polypeptides shown in SEQ ID NOs:1 and 2 were conjugated to HRPO. Diluted polypeptide:HRPO was added to each well (100 uL/well) and controls and serum samples (neat) were added (50 uL/well). A positive control for *E. chaffeensis* was used along with a negative control. The plates were tapped gently and incubated for 1 hour at RT. The plates were washed 6× with HW PetChek® wash buffer. 100 uL/well of TMB substrate was added to the wells and the plates were incubated for 10 min. 50 uL/well stop solution was added to the wells. The plates were read at A650. The negative cutoff was determined as 2× negative control O.D. value.

Example 2

Indirect ELISA Assay Plates and Protocols

Polypeptides shown in SEQ ID NOs:4, 5 and 6 were coated on Immulon® 1 plates. The coating buffer was 0.05M sodium carbonate, pH 9.6. 100 uL/well diluted peptide was added to the plates and the plates were incubated, covered, overnight at room temperature (RT). The polypeptides were aspirated and the plates were washed 2× with HW PetChek® wash buffer. 200 uL/well 2% TWEEN® (polysorbate) 20/2.5% sucrose in 0.1M Tris pH 7.6 was added to the wells and the plates were incubated, covered, for 2 hours at RT. The blocking solution was aspirated and the plates were tapped to remove excess liquid. The plates were dried in mylar bags overnight at RT with 2 (27 g) desiccants/6 plates. The plates were stored at 2° C.-8° C.

Diluted controls and serum samples were pipetted into the wells at 100 uL/well. A positive control for *E. chaffeensis* was used along with a negative control. The plates were incubated for 30 min. at RT. The plates were washed 5× with HW PetChek® wash buffer. 100 uL/well of diluted rabbit anti-dog:HRPO was added to the wells and incubated for 30 min. at RT. The plates were washed 5× with HW PetChek® wash buffer. 50 uL/well of TMB substrate was added to the plates and they were incubated for 10 min. 50 uL/well of stop solution was added. The plates were read at A650. The negative cutoff was determined as 2× negative control O.D. value.

The final optimum plate conditions for the indirect (a species) and direct (Ag:Ag) assay formats are shown in Table 1.

TABLE 1

| | | Indirect Assay Format | | | Direct Assay Format | |
|---|---|---|---|---|---|---|
| Analyte | Peptide | Coating [ug/ml] | Sample Dilution | Conjugate Dilution | Coating [ug/ml] | Conjugate [ug/ml] |
| *E. chaffeensis* | VLPT-1 | 1.0 | 1:50 | 1:1000 | 1.0 | 0.5 |
| *E. chaffeensis* | VLPT-R | 0.15 | 1:100 | 1:1000 | na | na |

Example 3

VLPT Polypeptide Assays

VLPT-1 (SEQ ID NO:5) and VLPT-2 (SEQ ID NO:6) were used in an indirect assay as described above to detect *E. chaffeensis* infection in *E. chaffeensis* infected and non-infected dogs. The positive samples (designated by "(+)") in Table 2 were field samples that were positive for *E. chaffeensis*, but negative for *E. canis*. The sample dilution was 1:100 and the rabbit anti-dog antibody dilution was 1:2000. The results are shown in Table 2. VLPT-1 and VLPT-2 accurately detected *E. chaffeensis* in the positive control and did not provide positive results for the negative samples and negative control. VLPT-1 yielded a positive result in 6 out of the 7 positive samples. VLPT-2 yielded a positive result in 5 out of the 7 positive samples.

TABLE 2

| | | VLPT-1 | | | VLPT-2 | | |
|---|---|---|---|---|---|---|---|
| | Sample | 0.25 | 0.5 | 1 | 0.25 | 0.5 | 1 |
| PC | 21349M | 0.628 | 0.669 | 0.765 | 0.157 | 0.193 | 0.176 |
| NC | 21172M | 0.038 | 0.034 | 0.036 | 0.034 | 0.040 | 0.039 |
| (+) | 21802F | 0.212 | 0.286 | 0.352 | 0.261 | 0.305 | 0.314 |
| | 22110F | 0.162 | 0.210 | 0.200 | 0.044 | 0.063 | 0.053 |
| | 21565F | 0.340 | 0.522 | 0.597 | 0.068 | 0.096 | 0.064 |
| | 21553F | 0.123 | 0.160 | 0.182 | 0.111 | 0.155 | 0.132 |
| | 22043F | 0.063 | 0.075 | 0.078 | 0.037 | 0.040 | 0.038 |
| | 22130F | 0.200 | 0.250 | 0.275 | 0.089 | 0.115 | 0.109 |
| | 22438M | 0.433 | 0.656 | 0.765 | 0.141 | 0.165 | 0.187 |
| (−) | 0349M | 0.039 | 0.039 | 0.036 | 0.038 | 0.046 | 0.045 |
| | 20934F | 0.047 | 0.047 | 0.042 | 0.042 | 0.050 | 0.051 |
| | 21608F | 0.041 | 0.042 | 0.040 | 0.046 | 0.044 | 0.041 |

VLPT-1 (SEQ ID NO:5) and VLPT-2 (SEQ ID NO:6) were used in a direct assay as described above to detect *E. chaffeensis* infection in *E. chaffeensis* infected and non-infected dogs. The positive samples (designated by "(+)") in Table 3 were field samples that were positive for *E. chaffeensis*, but negative for *E. canis*. The plates were coated at 0.5 and 1.0 ug/ml, the polypeptide:HRPO was tested at 0.5 and 1.0 ug/ml. The results are shown in Table 3. VLPT-1 and VLPT-2 accurately detected *E. chaffeensis* in the positive control and did not provide positive results for the negative samples and negative control. Both VLPT-1 and VLPT-2 yielded a positive result in 6 out of the 6 positive samples.

TABLE 3

| [Conj.] | VLPT-1 | | | | VLPT-2 | | | |
|---|---|---|---|---|---|---|---|---|
| | 0.5 | | 1 | | 0.5 | | 1 | |
| Sample | 0.5 | 1 | 0.5 | 1 | 0.5 | 1 | 0.5 | 1 |
| PC 21349M | 3.404 | 3.675 | 2.641 | 3.093 | 2.247 | 2.340 | 1.973 | 1.648 |
| NC 21172M | 0.038 | 0.041 | 0.049 | 0.046 | 0.040 | 0.043 | 0.049 | 0.043 |
| (+) 1177: 21A | 0.419 | 0.528 | 0.363 | 0.463 | 1.300 | 1.438 | 1.322 | 1.077 |
| 1177: 63D | 3.222 | 3.560 | 3.080 | 3.262 | 1.901 | 2.205 | 1.960 | 1.653 |
| 22438M | 1.893 | 2.049 | 1.697 | 1.843 | 1.152 | 1.486 | 1.154 | 1.311 |
| 22110F | 0.588 | 0.691 | 0.545 | 0.583 | 0.108 | 0.121 | 0.105 | 0.117 |
| 21846F | 0.263 | 0.301 | 0.244 | 0.282 | 0.433 | 0.426 | 0.357 | 0.337 |
| 22130F | 0.372 | 0.463 | 0.381 | 0.391 | 0.425 | 0.486 | 0.403 | 0.385 |
| (−) 3818: 57B | 0.042 | 0.042 | 0.063 | 0.053 | 0.038 | 0.041 | 0.048 | 0.044 |
| 3818: 58H | 0.035 | 0.041 | 0.051 | 0.049 | 0.037 | 0.038 | 0.036 | 0.037 |

VLPT-1 (SEQ ID NO:5) was used in a direct assay as described above to assay E. canis vaccinated dog samples. This assay was done to determine if VLPT-1 would provide a positive result in E. canis vaccinated dogs. The test samples were taken from the dogs after the second booster vaccination. The plates were coated at 1.0 ug/ml, the polypeptide: HRPO was used at a concentration of 0.5 ug/ml. The SNAP® 4Dx® assay was used to show that an anti-E. canis antibody response was induced in the vaccinated dogs. This assay screens for heartworm antigen, Ehrlichia canis antibody, Borrelia burgdorferi antibody and Anaplasma phagocytophilum antibody. The results are shown in Table 4. Positive results for E. canis antibody in the SNAP® 4Dx® test indicate that an antibody response was induced following vaccination. VLPT-1 does not provide a positive result when tested with samples from E. canis vaccinated dogs in direct assays. Therefore, VLPT-1 (SEQ ID NO:5) is specific for E. chaffeensis infection and does not react with sera from E. canis vaccinated dogs.

TABLE 4

| | | SNAP ® 4Dx ® for E. canis Ab | |
|---|---|---|---|
| Sample | | Signal minus backgrnd | VLPT-1 Direct |
| CVYDEH Ribi | Day 70 | N | 0.039 |
| | Day 105 | 0.07 (vw+) | 0.045 |
| | Day 112 | 0.17 | 0.036 |
| | Day 126 | 0.18 | 0.035 |
| CWMBDC Ribi | Day 70 | 0.08 | 0.036 |
| | Day 105 | 0.45 | 0.036 |
| | Day 112 | 0.40 | 0.037 |
| | Day 126 | 0.30 | 0.039 |
| CVXCSM Ribi | Day 70 | N | 0.035 |
| | Day 105 | N | 0.037 |
| | Day 112 | 0.14 | 0.035 |
| | Day 126 | 0.23 | 0.034 |
| CWMAXK Ribi + BCG | Day 70 | 0.07 (vw+) | 0.035 |
| | Day 105 | 0.26 | 0.035 |
| | Day 112 | 0.36 | 0.035 |
| | Day 126 | 0.34 | 0.035 |
| CVSCVA Ribi + BCG | Day 70 | 0.10 (w+) | 0.034 |
| | Day 105 | 0.51 | 0.037 |
| | Day 112 | 0.45 | 0.040 |
| | Day 126 | 0.47 | 0.036 |
| CVXCAP Ribi + BCG | Day 70 | N | 0.035 |
| | Day 105 | 0.51 | 0.034 |
| | Day 112 | 0.42 | 0.037 |
| | Day 126 | 0.48 | 0.035 |

VLPT-1 (SEQ ID NO:5) and VLPT-R (SEQ ID NO:4, where the X at position 112 is P) were used in an indirect assay as described above to assay experimentally E. canis-infected dog samples. This assay was done to determine if VLPT-1 and VLPT-R would result in a positive result in E. canis infected dogs. The plates were coated at 0.15 ug/ml (VLPT-R) and 1 ug/ml (VLPT-1). The sample dilution was 1:100 for VLPT-R and 1:50 for VLPT-1. The rabbit anti-dog: HRPO conjugate was used at a 1:1000 dilution. The results are shown in Table 5.

TABLE 5

| | | Plate (A650) | |
|---|---|---|---|
| | Sample | VLPT-R | VLPT-1 |
| (PC) | 1177: 21A | 2.298 | 0.379 |
| (NC) | 21172M | 0.046 | 0.048 |
| | Cutoff | 0.092 | 0.096 |
| E1 | d3 | 0.046 | 0.044 |
| | d21 | 0.047 | 0.046 |
| | d35 | 0.061 | 0.063 |
| E2 | d3 | 0.054 | 0.040 |
| | d21 | 0.105 | 0.059 |
| | d35 | 0.217 | 0.056 |
| E3 | d3 | 0.060 | 0.044 |
| | d21 | 0.065 | 0.043 |
| | d35 | 0.072 | 0.052 |
| E4 | d3 | 0.066 | 0.047 |
| | d21 | 0.051 | 0.049 |
| | d35 | 0.064 | 0.035 |
| E5 | d3 | 0.046 | 0.042 |
| | d21 | 0.057 | 0.038 |
| | d35 | 0.057 | 0.040 |
| E6 | d3 | 0.049 | 0.045 |
| | d21 | 0.046 | 0.075 |
| | d35 | 0.083 | 0.111 |

In general, VLPT-1 (SEQ ID NO:5) and VLPT-R (SEQ ID NO:4 where the X at position 112 is P) do not provide a positive result when tested with samples from E. canis infected dogs. However, both the VLPT-R and VLPT-1 have a single sample that shows slightly elevated levels on extended time points. However, these positive signals were weak compared to the positive control, and the signals did not increase with time post-vaccination as would be expected if true cross reaction with E. canis was occurring. Therefore, VLPT-1 and VLPT-R are specific for E. chaffeensis and not E. canis.

Figure 1B:
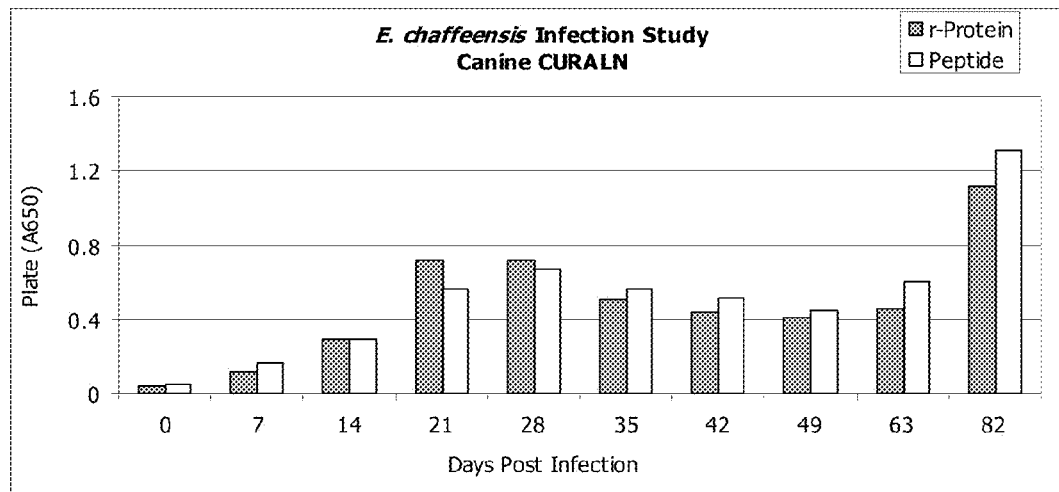

VLPT-1 (SEQ ID NO:5) and VLPT-R (SEQ ID NO:4 where the X at position 112 is P) were used in an indirect assay to test serum from E. chaffeensis experimentally infected dogs at several time points after infection. The plates were coated at 0.15 ug/mL for VLPT-R and at 1 ug/mL for VLPT-1. The sample dilution for VLPT-R was 1:100 and 1:50 for VLPT-1. The rabbit anti-dog:HRPO was used at a 1:1000 dilution. The results are shown in Table 6 and FIGS. 1A and 1B. Both VLPT-R and VLPT-1 were able to detect E. chaffeensis antibodies at least by day 7 post-infection.

TABLE 6

| | | VLPT-R | | VLPT-1 | |
|---|---|---|---|---|---|
| | Sample | A650 | Result | A650 | Result |
| CTUALJ | Pre-Bleed | 0.034 | N | 0.078 | N |
| | Day 7 | 0.562 | + | 0.482 | + |
| | Day 14 | 1.436 | + | 0.989 | + |
| | Day 21 | 1.192 | + | 0.926 | + |
| | Day 28 | 1.018 | + | 0.951 | + |
| | Day 35 | 0.782 | + | 0.594 | + |

TABLE 6-continued

|  | Sample | VLPT-R A650 | VLPT-R Result | VLPT-1 A650 | VLPT-1 Result |
|---|---|---|---|---|---|
|  | Day 42 | 0.559 | + | 0.779 | + |
|  | Day 49 | 0.449 | + | 0.897 | + |
|  | Day 56 | 0.422 | + | 0.743 | + |
|  | Day 63 | 0.225 | + | 0.619 | + |
|  | Day 77 | 0.497 | + | 0.285 | + |
|  | Day 96 | 1.470 | + | 1.318 | + |
| CURALN | Pre-Bleed | 0.044 | N | 0.044 | N |
|  | Day 7 | 0.113 | + | 0.163 | + |
|  | Day 14 | 0.292 | + | 0.293 | + |
|  | Day 21 | 0.717 | + | 0.562 | + |
|  | Day 28 | 0.721 | + | 0.665 | + |
|  | Day 35 | 0.509 | + | 0.559 | + |
|  | Day 42 | 0.437 | + | 0.510 | + |
|  | Day 49 | 0.403 | + | 0.448 | + |
|  | Day 63 | 0.452 | + | 0.601 | + |
|  | Day 82 | 1.117 | + | 1.305 | + |

VLPT-1 was used in direct assays to test known positive and negative field serum samples from dogs in a location of Arizona where *E. canis* found, but *E. chaffeensis* is absent. The plates were coated at 1 ug/mL and the peptide:HRPO was used at a concentration of 0.5 ug/mL. The results are shown in Table 7. VLPT-1 showed no positive results for the *E. canis* positive samples or the *E. canis* negative samples. Therefore, VLPT-1 is specific for *E. chaffeensis* antibodies and is not specific for *E. canis* antibodies.

TABLE 7

| Positive Samples: Ech VLPT-1 | | | Negative Samples: Ech VLPT-1 | | |
|---|---|---|---|---|---|
| Sample | A650 | Result | Sample | A650 | Result |
| HP-300 | 0.028 | N | HP-302 | 0.051 | N |
| HP-301 | 0.030 | N | HP-303 | 0.030 | N |
| HP-307 | 0.039 | N | HP-304 | 0.030 | N |
| HP-315 | 0.030 | N | HP-305 | 0.033 | N |
| HP-317 | 0.031 | N | HP-306 | 0.039 | N |
| HP-319 | 0.034 | N | HP-308 | 0.034 | N |
| HP-322 | 0.040 | N | HP-309 | 0.038 | N |
| HP-326 | 0.032 | N | HP-310 | 0.034 | N |
| HP-330 | 0.034 | N | HP-311 | 0.034 | N |
| HP-331 | 0.033 | N | HP-312 | 0.035 | N |
| HP-332 | 0.034 | N | HP-313 | 0.033 | N |
| HP-333 | 0.036 | N | HP-314 | 0.033 | N |
| HP-336 | 0.031 | N | HP-316 | 0.032 | N |
| HP-342 | 0.034 | N | HP-318 | 0.030 | N |
| HP-344 | 0.034 | N | HP-320 | 0.035 | N |
| HP-349 | 0.037 | N | HP-321 | 0.038 | N |
| HP-350 | 0.035 | N | HP-323 | 0.035 | N |
| HP-354 | 0.037 | N | HP-324 | 0.037 | N |
| HP-356 | 0.036 | N | HP-325 | 0.037 | N |
| HP-357 | 0.040 | N | HP-328 | 0.034 | N |
| HP-358 | 0.038 | N | HP-329 | 0.034 | N |
| HP-361 | 0.034 | N | HP-334 | 0.037 | N |
| HP-362 | 0.036 | N | HP-338 | 0.032 | N |
| HP-363 | 0.034 | N | HP-339 | 0.038 | N |
| HP-365 | 0.034 | N | HP-340 | 0.034 | N |
| HP-366 | 0.037 | N | HP-341 | 0.045 | N |
| HP-367 | 0.037 | N | HP-343 | 0.035 | N |
| HP-368 | 0.037 | N | HP-345 | 0.037 | N |
| HP-370 | 0.036 | N | HP-346 | 0.036 | N |
|  |  |  | HP-347 | 0.035 | N |
|  |  |  | HP-348 | 0.038 | N |
|  |  |  | HP-351 | 0.041 | N |
|  |  |  | HP-352 | 0.036 | N |
|  |  |  | HP-353 | 0.034 | N |
|  |  |  | HP-359 | 0.037 | N |
|  |  |  | HP-360 | 0.038 | N |
|  |  |  | HP-364 | 0.036 | N |
|  |  |  | HP-369 | 0.039 | N |

We claim:

1. A purified polypeptide comprising SEQ ID NO:3, wherein the polypeptide has less than 50 contiguous naturally occurring *Ehrlichia chaffeensis* amino acids.

2. The purified polypeptide of claim 1, wherein an amino acid occurs immediately before the amino acid at position 1 of SEQ ID N0:3, wherein the amino acid that occurs immediately before the amino acid at position 1 of SEQ ID NO:3 is C.

3. The purified polypeptide of claim 1, wherein the polypeptide consists of SEQ ID NO:3 or SEQ ID NO:6.

4. The purified polypeptide of claim 1, wherein the purified polypeptide is linked to an indicator reagent, an amino acid spacer, a signal sequence, a stop transfer sequence, a transmembrane domain, a protein purification ligand, a heterologous polypeptide, one or more additional polypeptides comprising SEQ ID NO:3 or SEQ ID NO:6, or a combination thereof.

5. The purified polypeptide of claim 1, wherein the purified polypeptide comprises one or more C amino acid residues at the amino terminus or carboxy terminus or both termini of the polypeptide.

6. A kit comprising the purified polypeptide of claim 1, and one or more of a substrate, a buffer, a control, an antibody, or an antibody fragment, for determining binding of the purified polypeptide to anti-*Ehrlichia chaffeensis* antibodies or antibody fragments in a sample.

7. The kit of claim 6, wherein the purified polypeptide is attached to a substrate.

8. A method of detecting antibodies that specifically bind an *Ehrlichia chaffeensis* polypeptide in a test sample, comprising:
（a) contacting a purified polypeptide comprising the polypeptide of claim 1 with the test sample, under conditions that allow polypeptide/antibody complexes to form;
(b) detecting the polypeptide/antibody complexes;
wherein the detection of the polypeptide/antibody complexes is an indication that antibodies specific for *Ehrlichia chaffeensis* are present in the test sample, and wherein the absence of the polypeptide/antibody complexes is an indication that antibodies specific for *Ehrlichia chaffeensis* are not present in the test sample.

9. The method of claim 8, further comprising contacting the complexes of step (a) with an indicator reagent prior to the performance of step (b).

10. The method of claim 8, wherein the purified polypeptide comprises SEQ ID NO:3 or SEQ ID NO:6 and wherein the method does not detect antibodies that specifically bind an *Ehrlichia canis* polypeptide.

11. The method of claim 8, wherein the amount of antibody in the test sample is determined.

12. The method of claim 8, wherein the purified polypeptide is attached to a substrate.

13. The method of claim 8, wherein the purified polypeptide is linked to an indicator reagent, an amino acid spacer, a signal sequence, a stop transfer sequence, a transmembrane domain, a protein purification ligand, a heterologous protein, one or more additional polypeptides comprising SEQ ID NO:3 or SEQ ID NO:6, or a combination thereof.

14. A method of detecting an *Ehrlichia chaffeensis* infection in a subject comprising:
(a) obtaining a biological sample from the subject;
(b) contacting a purified polypeptide comprising the polypeptide of claim 1 with the biological sample under conditions that allow polypeptide/antibody complexes to form;
(c) detecting the polypeptide/antibody complexes;
wherein the detection of the polypeptide/antibody complexes is an indication that the subject has an *Ehrlichia chaffeensis* infection.

15. The method of claim 14, wherein the purified polypeptide is SEQ ID NO:3 or SEQ ID NO:6 and wherein the method does not detect *Ehrlichia canis* infection in the subject.

16. The method of claim 14, further comprising contacting the complexes of step (b) with an indicator reagent prior to the performance of step (c).

17. The method of claim 14, wherein the amount of antibody in the test sample is determined.

18. The method of claim 14, wherein the purified polypeptide is attached to a substrate.

19. The method of claim 14, wherein the purified polypeptide is linked to an indicator reagent, an amino acid spacer, a signal sequence, a stop transfer sequence, a transmembrane domain, a protein purification ligand, a heterologous protein, one or more additional polypeptides comprising SEQ ID NO:3 or SEQ ID NO:6, or a combination thereof.

20. A purified polypeptide comprising SEQ ID NO:3, wherein the polypeptide comprises no more than 50 contiguous naturally occurring *Ehrlichia chaffeensis* amino acids.

21. The purified polypeptide of claim 20, wherein an amino acid occurs immediately before the amino acid at position 1 of SEQ ID NO:3, wherein the amino acid that occurs immediately before the amino acid at position 1 of SEQ ID NO:3 is C.

22. The purified polypeptide of claim 20, wherein the polypeptide consists of SEQ ID NO:3 or SEQ ID NO:6.

23. The purified polypeptide of claim 20, wherein the purified polypeptide is linked to an indicator reagent, an amino acid spacer, a signal sequence, a stop transfer sequence, a transmembrane domain, a protein purification ligand, a heterologous polypeptide, one or more additional polypeptides comprising SEQ ID NO:3 or SEQ ID NO:6, or a combination thereof.

24. The purified polypeptide of claim 20, wherein the purified polypeptide comprises one or more C amino acid residues at the amino terminus or carboxy terminus or both termini of the polypeptide.

* * * * *

SEQUENCE LISTING

```
<160> NUMBER OF SEQ ID NOS: 6

<210> SEQ ID NO 1
<211> LENGTH: 31
<212> TYPE: PRT
<213> ORGANISM: Ehrlichia chaffeensis
<220> FEATURE:
<221> NAME/KEY: MISC_FEATURE
<222> LOCATION: (1)..(1)
<223> OTHER INFORMATION: X can be any amino acid
<220> FEATURE:
<221> NAME/KEY: MISC_FEATURE
<222> LOCATION: (6)..(6)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be any amino acid
<220> FEATURE:
<221> NAME/KEY: MISC_FEATURE
<222> LOCATION: (8)..(8)
<223> OTHER INFORMATION: X can be any amino acid
<220> FEATURE:
<221> NAME/KEY: MISC_FEATURE
<222> LOCATION: (9)..(9)
<223> OTHER INFORMATION: X can be any amino acid
<220> FEATURE:
<221> NAME/KEY: MISC_FEATURE
```

```
<222> LOCATION: (13)..(13)
<223> OTHER INFORMATION: X can be any amino acid
<220> FEATURE:
<221> NAME/KEY: MISC_FEATURE
<222> LOCATION: (14)..(14)
<223> OTHER INFORMATION: X can be any amino acid
<220> FEATURE:
<221> NAME/KEY: MISC_FEATURE
<222> LOCATION: (22)..(22)
<223> OTHER INFORMATION: X can be any amino acid
<220> FEATURE:
<221> NAME/KEY: MISC_FEATURE
<222> LOCATION: (24)..(24)
<223> OTHER INFORMATION: X can be any amino acid
<220> FEATURE:
<221> NAME/KEY: MISC_FEATURE
<222> LOCATION: (26)..(26)
<223> OTHER INFORMATION: X can be any amino acid
<220> FEATURE:
<221> NAME/KEY: MISC_FEATURE
<222> LOCATION: (27)..(27)
<223> OTHER INFORMATION: X can be any amino acid
<220> FEATURE:
<221> NAME/KEY: MISC_FEATURE
<222> LOCATION: (28)..(28)
<223> OTHER INFORMATION: X can be any amino acid
<220> FEATURE:
<221> NAME/KEY: MISC_FEATURE
<222> LOCATION: (29)..(29)
<223> OTHER INFORMATION: X can be any amino acid
<220> FEATURE:
<221> NAME/KEY: MISC_FEATURE
<222> LOCATION: (30)..(30)
<223> OTHER INFORMATION: X can be any amino acid
<220> FEATURE:
<221> NAME/KEY: MISC_FEATURE
<222> LOCATION: (31)..(31)
<223> OTHER INFORMATION: X can be any amino acid

<400> SEQUENCE: 1

Xaa Ser Asp Leu His Xaa Xaa Xaa Xaa Val Glu Leu Xaa Xaa Pro Ser
 1               5                  10                  15

Lys Glu Glu Val Gln Xaa Glu Xaa Asp Xaa Xaa Xaa Xaa Xaa Xaa
             20                  25                  30

<210> SEQ ID NO 2
<211> LENGTH: 31
<212> TYPE: PRT
<213> ORGANISM: Ehrlichia chaffeensis
<220> FEATURE:
<221> NAME/KEY: MISC_FEATURE
<222> LOCATION: (7)..(7)
<223> OTHER INFORMATION: X can be any amino acid

<400> SEQUENCE: 2

Asp Ser Asp Leu His Gly Xaa Phe Ser Val Glu Leu Phe Asp Pro Ser
 1               5                  10                  15

Lys Glu Glu Val Gln Leu Glu Ser Asp Leu Gln Gln Ser Ser Asn
             20                  25                  30

<210> SEQ ID NO 3
<211> LENGTH: 31
<212> TYPE: PRT
<213> ORGANISM: Ehrlichia chaffeensis
<220> FEATURE:
<221> NAME/KEY: MISC_FEATURE
<222> LOCATION: (7)..(7)
<223> OTHER INFORMATION: X can be any amino acid

<400> SEQUENCE: 3

Asn Ser Asp Leu His Glu Xaa Ser Phe Val Glu Leu Pro Gly Pro Ser
 1               5                  10                  15
```

-continued

Lys Glu Glu Val Gln Phe Glu Asp Asp Ala Lys Asn Val Val Tyr
20 25 30

<210> SEQ ID NO 4
<211> LENGTH: 177
<212> TYPE: PRT
<213> ORGANISM: Ehrlichia chaffeensis
<220> FEATURE:
<221> NAME/KEY: MISC_FEATURE
<222> LOCATION: (112)..(112)
<223> OTHER INFORMATION: X can be any amino acid

<400> SEQUENCE: 4

Met Ser Gln Phe Ser Glu Asp Asn Ile Gly Asn Ile Gln Met Pro Phe
1 5 10 15

Ser Asn Leu Gln Glu Ser Ser His Leu Glu Leu Pro Ser Leu Ser Glu
20 25 30

Lys Val Ile His Leu Glu Ser Gly Leu Gln Gln Ser Ser Asp Ser Asp
35 40 45

Ser His Glu Pro Ser His Leu Glu Leu Pro Ser Leu Ser Glu Glu Val
50 55 60

Ile Gln Leu Glu Ser Asp Leu Gln Gln Ser Ser Asn Ser Asp Leu His
65 70 75 80

Gly Ser Phe Ser Val Glu Leu Phe Asp Pro Phe Lys Glu Ala Val Gln
85 90 95

Leu Gly Asn Asp Leu Gln Gln Ser Ser Asp Ser Asp Leu His Gly Xaa
100 105 110

Phe Ser Val Glu Leu Phe Asp Pro Ser Lys Glu Glu Val Gln Leu Glu
115 120 125

Ser Asp Leu Gln Gln Ser Ser Asn Ser Asp Leu His Glu Ser Ser Phe
130 135 140

Val Glu Leu Pro Gly Pro Ser Lys Glu Glu Val Gln Phe Glu Asp Asp
145 150 155 160

Ala Lys Asn Val Val Tyr Gly Gln Asp His Val Ser Leu Ser Glu Leu
165 170 175

Gly

<210> SEQ ID NO 5
<211> LENGTH: 32
<212> TYPE: PRT
<213> ORGANISM: Ehrlichia chaffeensis

<400> SEQUENCE: 5

Cys Asp Ser Asp Leu His Gly Pro Phe Ser Val Glu Leu Phe Asp Pro
1 5 10 15

Ser Lys Glu Glu Val Gln Leu Glu Ser Asp Leu Gln Gln Ser Ser Asn
20 25 30

<210> SEQ ID NO 6
<211> LENGTH: 32
<212> TYPE: PRT
<213> ORGANISM: Ehrlichia chaffeensis

<400> SEQUENCE: 6

Cys Asn Ser Asp Leu His Glu Ser Ser Phe Val Glu Leu Pro Gly Pro
1 5 10 15

Ser Lys Glu Glu Val Gln Phe Glu Asp Asp Ala Lys Asn Val Val Tyr
20 25 30